US 11,370,813 B2

(12) United States Patent
Zhao

(10) Patent No.: US 11,370,813 B2
(45) Date of Patent: Jun. 28, 2022

(54) PEPTOID, AND ITS PREPARATION METHOD AND USE

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Zijian Zhao, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 206 days.

(21) Appl. No.: 16/642,572

(22) PCT Filed: Oct. 10, 2019

(86) PCT No.: PCT/CN2019/110442
§ 371 (c)(1),
(2) Date: Feb. 27, 2020

(87) PCT Pub. No.: WO2020/140529
PCT Pub. Date: Jul. 9, 2020

(65) Prior Publication Data
US 2021/0188908 A1    Jun. 24, 2021

(30) Foreign Application Priority Data
Jan. 3, 2019   (CN) .......................... 201910005412.7

(51) Int. Cl.
| A61K 31/165 | (2006.01) |
| C07K 7/06 | (2006.01) |
| B01L 3/00 | (2006.01) |
| C07K 1/04 | (2006.01) |
| C07K 1/06 | (2006.01) |
| G01N 33/68 | (2006.01) |
| A61K 38/00 | (2006.01) |

(52) U.S. Cl.
CPC .............. *C07K 7/06* (2013.01); *B01L 3/5027* (2013.01); *C07K 1/04* (2013.01); *C07K 1/06* (2013.01); *G01N 33/68* (2013.01); *A61K 38/00* (2013.01); *G01N 2800/52* (2013.01)

(58) Field of Classification Search
None
See application file for complete search history.

(56) References Cited

U.S. PATENT DOCUMENTS

2021/0206808 A1* 7/2021 Zhao .................... G01N 33/574

* cited by examiner

*Primary Examiner* — Fred H Reynolds
(74) *Attorney, Agent, or Firm* — Dilworth & Barrese, LLP.; Michael J. Musella, Esq.

(57) ABSTRACT

The embodiments disclosed herein provide a peptoid, which is a compound of Formula I or a stereoisomer, a mixture of stereoisomers, or a pharmaceutically acceptable salt thereof. $N-R_4$, $N-R_3$, $N-R_2$, and $N-R_1$ in Formula I are respectively. The peptoid has a strong binding ability with EGFR protein. It can be used not only for targeted treatment of diseases associated with EGFR protein, but also for imaging detection or prognosis monitoring of diseases associated with EGFR protein.

Formula I

17 Claims, 1 Drawing Sheet

PEPTOID, AND ITS PREPARATION METHOD AND USE

This application claims priority to Chinese Patent Application No. 201910005412.7, filed on Jan. 3, 2019, which is incorporated herein by reference in its entirety as part of this application.

TECHNICAL FIELD

The present disclosure relates to the technical field of biomedicine. In particular, embodiments disclosed herein relate to a peptoid, and its preparation method and use.

BACKGROUND

A human epithelial growth factor receptor (HER) family is a transmembrane tyrosine kinase, including four members: EGFR/ErbB1/HER1, ErbB2/HER2, ErbB3/HER3, and ErbB4/HER4. Overexpression, mutation or gene amplification of these members may cause many malignancies.

Mini-Reviews in Medicinal Chemistry, 2016, 16, 1134-1166 discloses that normal cells express EGFR in a range of 40,000 to 100,000 receptors/cell, while in some breast cancers, the expression level reaches $2 \times 10^6$ EGFR molecules/cell. It has been found that various cancers such as breast cancer, kidney cancer, colon cancer, rectal cancer, lung cancer, ovarian cancer, head and neck cancer, bladder cancer, pancreatic cancer and glioma are involved in overexpression of EGFR (see Current Protein and Peptide Science, 2018, 19, 380-388). EGFR has become an important target for the treatment of these tumors.

Targeted cancer treatment and in vivo imaging have become one of the most popular topics in the academic and clinical medical fields. Traditionally, the anti-tumor drugs currently used in clinical practice are mainly cytotoxic chemotherapy drugs, but these drugs have poor selectivity, large toxic and side effects, and easily cause adverse reactions. Although protein drugs such as antibodies have high specificity and small toxic and side effects, they can easily cause immune response and produce drug resistance due to their large molecular mass and complex structure. Moreover, preparation process of protein drugs is so complicated that they are too expensive for ordinary tumor patients to bear.

With the enhanced permeability and retention effect (EPR) of solid tumors, new drug carriers can deliver drugs to tumor sites in a passively targeted manner Specific targeted drug delivery requires specific recognition elements to enable drugs to be actively enriched at the tumor site, thereby increasing the drug concentration, increasing penetration, and significantly improving efficacy. Moreover, in vivo imaging can be achieved by using recognition elements as a main body and combining imaging methods such as fluorescence and nuclear magnetic resonance. Therefore, the recognition element is very important for the entire targeted drug and in vivo imaging, in which the recognition element includes antibodies, polypeptides/peptoids, and aptamers, and other molecular probes that target specific receptor proteins at tumor sites. Among various targeting molecules, small molecule aptamers have a series of unique advantages, such as low immunogenicity, good tissue permeability, small molecular weight, high stability, easy modification and low cost.

Studies have shown that high heterogeneity and variable plasticity of the expression of different receptors in the HER family lead to poor clinical treatment effects and drug resistance. Due to the tumor heterogeneity and resistance to multiple drugs caused by diverse expression patterns of the HER family, drug delivery via the EPR effect alone limits the amount of drugs accumulated in such tumors and the therapeutic effect. Recent studies have found that the use of bispecific ligands to recognize multiple tumor markers will significantly improve the stability and reliability of tumor diagnosis and treatment, especially targeted delivery for heterogeneous tumors. Compared with monotherapy, a combined treatment of targeted inhibition of tumor growth, invasion and metastasis is more effective in improving the treatment effect, reducing drug toxicity and overcoming drug resistance.

Therefore, there is still a need to develop a molecular probe for targeted therapy, imaging detection, or prognosis monitoring of diseases associated with EGFR protein.

SUMMARY

At least one embodiment disclosed herein provides a peptoid, which is a compound of Formula I, or a stereoisomer, a mixture of stereoisomers, or a pharmaceutically acceptable salt thereof,

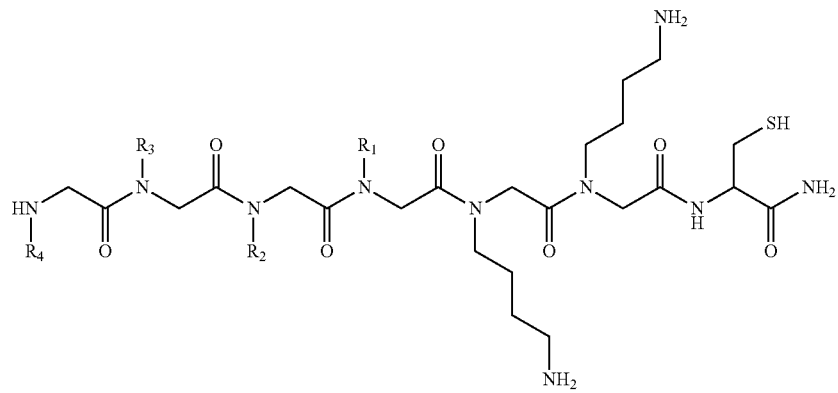

Formula I wherein N—R$_4$, N—R$_3$, N—R$_2$, and N—R$_1$ in Formula I are

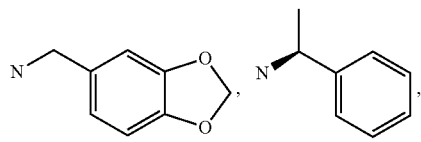

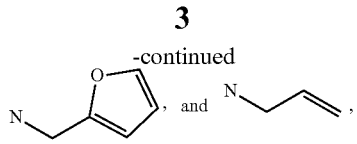

respectively.

For example, among the peptoids, the pharmaceutically acceptable salt is hydrochloride, nitrate, sulfate, phosphate, formate, acetate, fumarate, maleate, citrate, succinate, tartrate, mesylate, or p-toluenesulfonate.

In one embodiment, the peptoid is the compound of Formula I.

At least one embodiment disclosed herein also provides a method for preparing a peptoid, the method including:
(1) carrying out an amidation reaction between a compound of Formula II and an amino group at a terminal end of a solid phase support resin to form an amide bond;

Formula II wherein R is OH or Cl;
(2) adding a monomer to replace the bromine atom through a nucleophilic substitution reaction;
(3) repeating steps (1) and (2) until the synthesis of all subunits is completed,
wherein the monomers are added in an order of cysteine, monoprotected tetramethylenediamine, monoprotected tetramethylenediamine, allylamine, 2-aminomethylfuran, α-methylbenzylamine, and 3,4-methylenedioxybenzylamine, wherein the wording "monoprotected" means that one amino group in the diamine is protected by an amino protecting group; and
(4) removing the amino protecting group on the side chain, and cleaving the peptoid from the resin.

For example, the α-methylbenzylamine used can be R(+)-α-methylbenzylamine

At least one embodiment disclosed herein provides the use of any of the above-mentioned peptoids in the manufacture of a medicament for the targeted treatment of a disease associated with EGFR protein.

For example, the disease associated with EGFR protein is breast cancer, kidney cancer, colon cancer, rectal cancer, lung cancer, ovarian cancer, head and neck cancer, bladder cancer, pancreatic cancer, or glioma. In one embodiment, the disease associated with EGFR protein is non-small cell lung cancer.

At least one embodiment disclosed herein also provides a pharmaceutical composition comprising any of the above-mentioned peptoids; and a pharmaceutically acceptable adjuvant.

For example, the adjuvant is any one or more of excipients, diluents, carriers, flavoring agents, binders, and fillers.

At least one embodiment disclosed herein also provides the use of any of the above-mentioned pharmaceutical compositions for imaging detection or prognostic monitoring of diseases associated with EGFR protein.

For example, the disease associated with EGFR protein is colon cancer, rectal cancer, lung cancer, ovarian cancer or head and neck cancer. In one embodiment, the disease associated with EGFR protein is non-small cell lung cancer.

At least one embodiment disclosed herein also provides a chip comprising any of the above-mentioned peptoids. For example, the peptoid is coupled to the surface of the chip. In one embodiment, the chip is a microfluidic chip.

At least one embodiment disclosed herein also provides a kit for identifying circulating tumor cells, including a box body, and the above-mentioned microfluidic chip disposed in the box body.

BRIEF DESCRIPTION OF THE DRAWINGS

In order to more clearly illustrate the technical solutions of embodiments disclosed herein, the drawings of embodiments will be briefly introduced below. Obviously, the drawings described below only relate to some embodiments disclosed herein, but do not limit the present disclosure.

DETAILED DESCRIPTION

Figure 1:
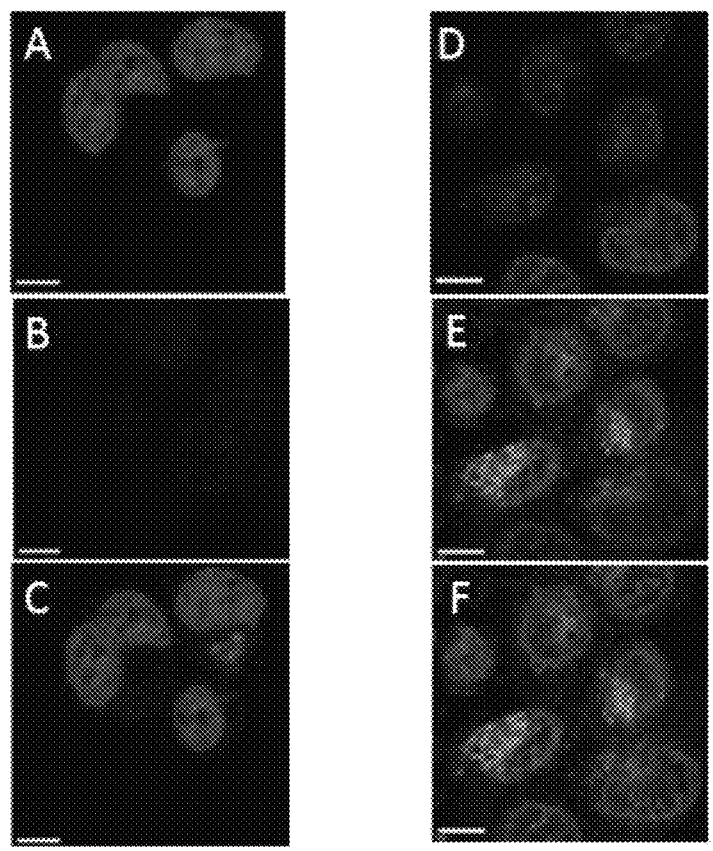
FIG. 1 is a graph showing the result of cell-level imaging using a fluorescently labeled molecular probe with the peptoid of Example 1.

The various documents and publications mentioned in this disclosure are incorporated herein by reference. Unless otherwise defined, the technical or scientific terms used in this disclosure shall have the ordinary meaning as understood by those of ordinary skill in the art to which this invention belongs.

The term "pharmaceutically acceptable" in this disclosure indicates that a substance or composition is chemically and/or toxicologically compatible with other ingredients that make up the formulation and/or the mammal being treated therewith. The term "pharmaceutically acceptable salt" in this disclosure refers to a pharmaceutically acceptable salt formed by a compound.

The word "including", "containing", "comprising", or the like used in this disclosure indicates that the element appearing before the word encompasses the element listed after the word and its equivalent, without excluding other elements. A monomer in the present disclosure refers to an amine added as a raw material in the solid-phase synthesis of a peptoid. A subunit in the present disclosure refers to a structural unit constituting a peptoid.

A peptoid is a polypeptide mimetic with an N-substituted glycine as a structural unit. Compared with a polypeptide, side chains of a peptoid are transferred from α-carbon to nitrogen. Different from traditional polypeptides which are composed of only 20 kinds of amino acids, the peptoid is synthesized by a monomer synthesis process and its constituent units are determined by different amines There are thousands of amines, and thus the peptoids have extremely abundant sequences. It is possible to develop different chemical sequence structures for different targets. Moreover, because the peptoids are not recognized by enzymes, the peptoids can effectively resist proteolysis in vivo, which makes the peptoids have more obvious advantages as a molecular probe.

The drug delivery system and the molecular imaging system developed based on the peptoid molecular probe may enhance the stability of drugs, increase an interaction between drugs and tumor cells/tissues, and increase the circulating metabolic cycle in vivo. Therefore, it has advantages in terms of in vivo imaging diagnosis, drug efficacy enhancement, overcoming of drug resistance, and reduction of toxicity side effects.

The present disclosure provides a peptoid, which is a compound of Formula I, or a stereoisomer, a mixture of stereoisomers, or a pharmaceutically acceptable salt thereof,

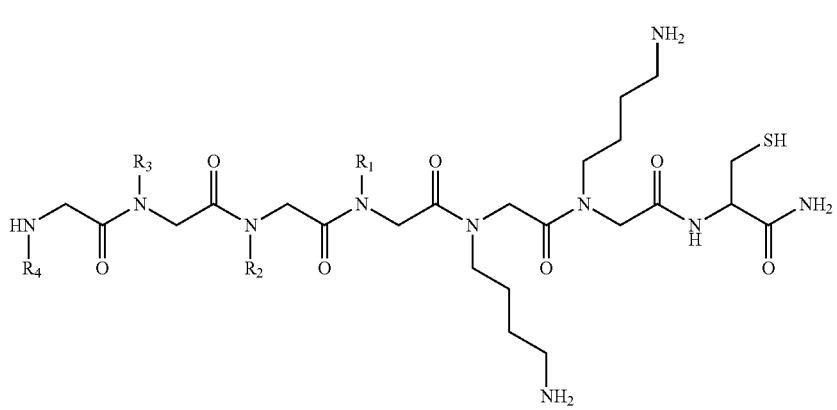

Formula I wherein N—R$_4$, N—R$_3$, N—R$_2$, and N—R$_1$ in Formula I are

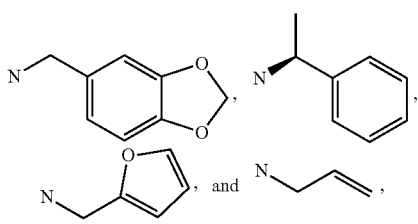

respectively.

The term "stereoisomer" belongs to a kind of isomers, and refers to an isomer that has the same interconnecting orders of atoms or atomic groups, but different spatial arrangements.

With regard to the stereoisomer, the compound of Formula I has two asymmetric carbon atoms, and can exist as individual enantiomers or diastereomers, or as their mixture. The compound of Formula I or a pharmaceutically acceptable salt thereof may be used in the form of racemic mixtures, diastereomeric mixtures, enantiomerically enriched mixtures, diastereomerically enriched mixtures, or enantiomerically and diastereomerically pure individual stereoisomers. The present disclosure encompasses any stereoisomer of the compound of Formula (I) or a pharmaceutically acceptable salt thereof, and a mixture thereof.

The peptoid disclosed herein can be prepared as individual enantiomers or diastereomers or mixtures thereof by selecting raw materials. For example, in the preparation of a peptoid disclosed herein, the α-methylbenzylamine as a raw material can be selected from R(+)-α-methylbenzylamine, S(−)-α-methylbenzylamine, or a mixture of the two, and the cysteine as a raw material can be selected from D-cysteine, L-cysteine, or a mixture of the two.

The peptoid disclosed herein can also be separated into individual enantiomers or diastereomers by chiral resolution, such as chiral HPLC resolution.

In one embodiment disclosed herein, the peptoid is the compound of Formula I.

The peptoid disclosed herein may exist in the form of a salt. For example, the salt may be prepared by reacting a peptoid compound with an inorganic or organic acid. The inorganic acid is, for example, hydrochloric acid, hydrobromic acid, sulfuric acid, nitric acid, phosphoric acid, or the like. The organic acid is, for example, formic acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, mesylic acid, ethanesulfonic acid, p-toluenesulfonic acid, salicylic acid, or the like.

In one embodiment disclosed herein, the salt is a pharmaceutically acceptable salt. For example, the pharmaceutically acceptable salt may be hydrochloride, hydrobromide, sulfate, nitrate, phosphate, formate, acetate, propionate, fumarate, glycolate, pyruvate, malate, malonate, benzoate, cinnamate, mandelate, salicylate, maleate, citrate, succinate, tartrate, mesylate, ethanesulfonate, or p-toluenesulfonate.

In one embodiment disclosed herein, the pharmaceutically acceptable salt is, for example, hydrochloride, nitrate, sulfate, phosphate, formate, acetate, fumarate, maleate, citrate, succinate, tartrate, mesylate, or p-toluenesulfonate.

The present disclosure also provides a method for preparing the above-mentioned peptoid. The peptoid disclosed herein can be synthesized by a solid-phase synthesis method according to the subunit order of Formula I. The solid-phase synthesis method is well known to those skilled in the art. For example, J. Am. Chem. Soc. 1992, 114, 10646-10647 reports a method for solid phase synthesis of peptoid. The peptoid disclosed herein can be synthesized by the solid phase synthesis method shown below.

Reaction 1

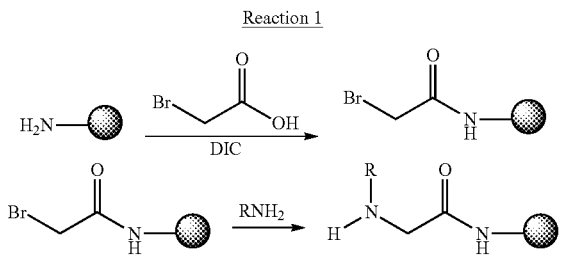

In the above reaction 1, bromoacetic acid may be replaced with bromoacetyl chloride.

At least one embodiment disclosed herein also provides a method for preparing a peptoid. The method includes:
(1) carrying out an amidation reaction between a compound of Formula II and an amino group at a terminal end of a solid phase support resin to form an amide bond;

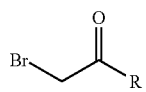

Formula II wherein R is OH or Cl;
(2) adding a monomer to replace the bromine atom through a nucleophilic substitution reaction;
(3) repeating steps (1) and (2) until the synthesis of all subunits is completed, wherein the monomers are added in an order of cysteine, monoprotected tetramethylenediamine, monoprotected tetramethylenediamine, allylamine, 2-aminomethylfuran, α-methylbenzylamine, and 3,4-methylenedioxybenzylamine, wherein the wording "monoprotected" means that one amino group in the diamine is protected by an amino protecting group; and
(4) removing the amino protecting group on the side chain, and cleaving the peptoid from the resin.

In a method for preparing a peptoid according to an embodiment disclosed herein, the α-methylbenzylamine monomer may be selected from R(+)-α-methylbenzylamine, S(−)-α-methylbenzylamine, or a mixture of the two, and the cysteine monomer may be selected from D-cysteine, L-cysteine, or a mixture of the two. For example, the α-methylbenzylamine monomer may be selected from R(+)-α-methylbenzylamine. For example, the cysteine monomer can be selected from L-cysteine.

In the method for preparing a peptoid disclosed herein, firstly, the compound of Formula II is subjected to an amidation reaction with an amino group at the terminal end of a solid phase support resin to form an amide bond, and then a subsequent nucleophilic substitution reaction with a monomer is carried out, and the compound of Formula II is again used to carry out an amidation reaction with an amino group of the previous monomer to form an amide bond, and the subsequent nucleophilic substitution reaction with another monomer is carried out until the synthesis of all subunits is completed.

As an amino-protecting group, amino-protecting groups known in the art for the synthesis of proteins, polypeptides, or peptoids can be used without limitation, for example, amino protecting groups listed in Greene's Protective Groups in Organic Synthesis, 5th edition by Peter G. M. Wuts. In some embodiments, the amino protecting group is 9-fluorenylmethoxycarbonyl (Fmoc) or tert-butoxycarbonyl (Boc). For example, in some embodiments, the amino protecting group is tert-butoxycarbonyl.

The reaction conditions of the amidation reaction in the above step (1) are not particularly limited, and conventional conditions for an amidation reaction for the synthesis of proteins, polypeptides, or peptoids in the art may be adopted, as long as the amino group can be acylated without disrupting the function of the peptoid. For example, the amidation reaction described above can be carried out in the presence of a condensation agent. The condensation agent may be, without limitation, a condensation agent known in the art for the synthesis of proteins, polypeptides, or peptoids. For example, the condensation agent may be a carbodiimide-based condensation agent, for example, N,N'-diisopropylcarbodiimide (DIC), N,N'-dicyclohexylcarbodiimide (DCC), 1-ethyl-(3-dimethylaminopropyl)carbodiimide (EDC) and so on; a benzotriazole-based condensation agent, for example, 1-hydroxylbenzotriazole(HOBt); a benzenesulfonylchloride-based condensation agent, for example, tri-isopropylbenzenesulfonyl chloride (TPS) and so on; a succinimide-based condensation agent, for example, disuccinimido carbonate (DSC), succinimido diphenyl phosphate (SDPP) and so on; 2-ethoxy-1-ethoxycarbonyl-1,2-dihydroquinoline (EEDQ); 3-(diethoxyphosphoryloxy)-1,2,3-benzotriazin-4(3H)-one (DEPBT) and so on.

The reaction conditions of the nucleophilic substitution reaction in the above-mentioned step (2) are not particularly limited, and conventional nucleophilic substitution conditions for using in the synthesis of proteins, polypeptides, or peptoids can be used, as long as the bromine atom can be replaced and the function of the peptoid is not damaged. For example, the reaction is carried out at a temperature of 35° C. to 40° C. for 30 minutes or more, 60 minutes or more, or 90 minutes or more.

In the above-mentioned step (4), the removal of the side chain amino protection group and the cleavage of the peptoid from the resin can be carried out simultaneously or successively. For example, firstly, the peptoid is cleaved from the resin, and then the side chain amino protection group is removed; alternatively, the side chain amino protection group is removed firstly, and then the peptoid is cleaved from the resin; or the peptoid is cleaved from the resin while the side chain amino protection group is removed. The conventional conditions for synthesis of proteins, polypeptides or peptoids in the art can be used to remove the side chain amino protection group and cleave the peptoid from the resin, as long as the purpose can be achieved and the function of the peptoid is not damaged. In an embodiment, the peptoid is cleaved from the resin while the side chain amino protection group is removed by a cleaving solution containing 95% trifluoroacetic acid, 2.5% ultrapure water and 2.5% trisisopropylsilane at a volume ratio.

In a method for preparing a peptoid disclosed herein, a step of purifying the obtained product may be further included as necessary. The purification method is not particularly limited, and methods known in the art for purifying corresponding similar products, such as precipitation, filtration, dialysis, gel permeation chromatography, HPLC, and the like, can be used.

The present disclosure also provides a medicament for the targeted treatment of diseases associated with EGFR protein. The peptoid disclosed herein can specifically recognize the EGFR protein, and therefore, it can be used as a molecular probe that specifically recognizes the EGFR protein for preparing a medicament for the targeted treatment of a disease associated with the EGFR protein. For example, the disease associated with EGFR protein is breast cancer, kidney cancer, colon cancer, rectal cancer, lung cancer, ovarian cancer, head and neck cancer, bladder cancer, pancreatic cancer, or glioma. In one embodiment, the disease associated with EGFR protein is non-small cell lung cancer.

The present disclosure also provides a pharmaceutical composition comprising any of the above-mentioned peptoids and a pharmaceutically acceptable adjuvant. For example, the pharmaceutically acceptable adjuvant is any one or more of excipients, diluents, carriers, flavoring agents, binders and fillers.

The peptoids disclosed herein have a very high affinity for EGFR protein, and thus can realize targeted drug delivery and localized imaging by identifying the EGFR protein, thereby providing a new option for the diagnosis and treatment of diseases with high expression of EGFR, and also providing live data evidence for sequencing and digital PCR results.

The present disclosure also provides the use of the above-mentioned pharmaceutical composition for imaging detection or prognosis monitoring of diseases associated with EGFR protein. For example, the diseases associated with EGFR protein are colon cancer, rectal cancer, lung cancer, ovarian cancer, or head and neck cancer. In one embodiment, the disease associated with EGFR protein is non-small cell lung cancer.

The present disclosure also provides a chip (e.g., a microfluidic chip) containing the above-mentioned peptoid. In one embodiment, the peptoid is coupled to the chip surface for the capture and diagnosis of circulating tumor cells.

Circulating tumor cell (CTC) is a collective name for various types of tumor cells that exist in peripheral blood. It is detached from solid tumor lesions (primary lesions, metastases) spontaneously or due to diagnosis or treatment operation. Most CTCs undergo apoptosis or are swallowed after entering the peripheral blood. A few can escape and develop into metastases, increasing the risk of death in patients with malignant tumors. The presence or absence of CTC and the amount of CTC are important indicators of cancer progression and metastasis. Detection and tracking of the amount of CTCs in peripheral blood is helpful for early screening, efficacy monitoring, prognostic judgment and recurrence prediction of patients.

The detection technology for CTCs can predict the occurrence of early tumors, and can detect the tumor metastasis during treating patients with drugs. In addition, it can also guide medication for subsequent treatment. CTCs are derived from primary tumors or metastatic tumors. CTCs can enter blood vessels after being detached from basement membrane. Because the content of CTCs in the blood is extremely low and its size is similar to the size of white blood cells, CTCs are difficult to be detected using liquid biopsy technology. However, CTCs carry relevant cancer-specific, highly expressed proteins on their surfaces.

The chip disclosed herein can be prepared in accordance with conventional methods by using various blank chips known in the prior art for capturing and detecting CTCs; or can be prepared by using commercially available blank chips that can be used for capturing and detecting CTCs. For example, the chip can be prepared from a PlexArray HT 3D chip available from Plexera Bioscience, USA.

Coupling of peptoid on a chip surface can be achieved by formulating the peptoid into a sample of a peptoid molecule probe, spotting it on the chip surface, and then incubating.

By being combined with surface plasmon resonance imaging technology, the chip disclosed herein can realize the capture and diagnosis of CTCs of diseases associated with EGFR protein, such as colon cancer, rectal cancer, lung cancer, ovarian cancer, or head and neck cancer.

The present disclosure also provides a kit for identifying circulating tumor cells, comprising a box body, a microfluidic chip disposed in the box body, and a fluorescent probe disposed in the box body, wherein the fluorescent probe is the above-mentioned peptoid with a fluorescent label.

For example, the microfluidic chip includes a microvalve control layer and a microvalve film layer. The microvalve control layer is provided with three gas channels, as well as six holes through the control layer. The three holes are sample loading holes, which are communicated with a substrate and used for inflow and outflow of samples and reagents; and the other three holes are connected to the three gas channels, respectively, for gas injection and to control the opening and closing of microvalve. The microvalve film layer is provided with three holes through the film layer, which are communicated with the three sample loading holes of the above-mentioned microvalve control layer, respectively.

For example, the outline dimensions of the microvalve control layer and the microvalve film layer should match the substrate.

The type of the fluorophore used for fluorescent labeling is not particularly limited, as long as the modification can impart fluorescent properties to the peptoid and the modified peptoid can also realize the basic function of the peptoid. The peptoid can be modified with one or more fluorophores. For example, a single fluorescently labeled peptoid is obtained by modification with one fluorophore, or a double fluorescently labeled peptoid is obtained by modification with two fluorophores. In some embodiments, the fluorophore may be selected from, without limitation, blue fluorescent dyes, near-infrared fluorescent dyes, green fluorescent dyes, and the like, e.g. coumarin-containing fluorophores, anthracene-containing fluorophores, rhodamine fluorophores, phenanthrenoimidazole fluorophores, naphthalene-containing fluorophores, fluorescein isothiocyanate, carboxyfluorescein (FAM), fluorescein thiocyanate (FITC), dansyl chloride, 2,4-dinitrophenylhydrazine (Dnp), carboxyrhodamine 110, Texas Red, pentamethine cyanine dyes (Cy5), heptamethine cyanine dyes (Cy7), etc. In one embodiment, the fluorescent dye is selected from Rhodamine B. For example, fluorescently labeled peptoids are obtained by adding peptoids to HBTU at 1:1, adding Rhodamine B, and then reacting for 3 hours.

For example, in addition to microfluidic chips and fluorescent probes, the detection system can also include a fluorescence microscope (fluorescence imaging system), an image analysis software (analysis counting system), and a pump to form a complete system so as to process blood samples and isolate and count circulating tumor cells.

For example, a fluorescence microscope is used to detect whether cells in a micro-location array have fluorescence, and a full-coverage fluorescence imaging is performed on the functional area to obtain a multi-channel fluorescence image.

For example, an image processing software is used to analyze the images acquired by a fluorescence microscope and obtain the corresponding amount of CTCs. The software screens out CTCs that meet requirements by accurately calculating the size, area, aspect ratio, and roundness of cells in the image, and counts the CTCs. The localized cells can be screened and identified according to an algorithm. Circulating tumor cells that meet the labelled fluorescent characteristics are identified and counted, the cell location is reported, and the cell image is magnified.

Unless otherwise specified, the experimental methods used in the following examples are conventional methods. Unless otherwise specified, the materials and reagents used in the following examples can be obtained from commercial sources.

The SPRi instrument in the following examples is Plexera Kx5V2, Plexera Bioscience LLC, USA. The instrument is mainly equipped with a 660 nm LED light source, a CCD image collector and a sensor chip with a microfluidic channel. The instrument displays the change of the reflected light intensity over time at each monitoring point and records it as an SPR curve.

Unless otherwise specified, "EGFR" herein refers to the full-length human epidermal growth factor receptor 1.

Unless otherwise specified, "nM" herein refers to "n mol/L", "μM" refers to "p, mol/L", and "mM" refers to "m mol/L".

Example 1 Preparation of a Peptoid of Formula I

The peptoids were synthesized by solid-phase synthesis, comprising the following steps:

(1) immersing Rink amide AM resin (having a substitution level of 0.3 mmol/g, 200 mg) in N,N-dimethylformamide (DMF), and discharging the DMF solution after 15 minutes of full swelling;
(2) deprotection: formulating a DMF solution comprising 20% of hexahydropyridine, and immersing the resin into an excessive amount of the deprotection solution for 10 min, so as to remove the protection group Fmoc and expose the free amino;
(3) washing the resin: washing the resin alternately with dichloromethane (DCM) and DMF for three times each;
(4) adding 2 M of bromoacetic acid in DMF (2.5 ml) and 3.2 M of N,N'-diisopropylcarbodiimide (DIC) in DMF (2.5 ml) to the Rink amide AM resin, and reacting at 37° C. for 30 min to acylate the terminal amino of the resin;
(5) further adding a 2 M solution of a monomer in DMF (5 ml), and reacting at 37° C. for 90 min, so as to replace the bromine atom by a nucleophilic substitution reaction, thereby completing the synthesis of a subunit;
(6) washing the resin: washing the resin alternately with DCM and DMF for three times each;
(7) repeating steps (4) to (6) until the synthesis of other subunits was completed; wherein the order of adding the monomers was: L-cysteine; Boc-protected tetramethylenediamine; Boc-protected tetramethylenediamine; allylamine; 2-aminomethylfuran; R(+)-α-methylbenzylamine; and 3,4-methylenedioxybenzylamine;
(8) removing the side-chain protection group at the end of the synthesis, and cleaving the peptoid from the resin by treatment with 95% trifluoroacetic acid, 2.5% ultrapure water and 2.5% triisopropylsilane for 2 hours; and
(9) purifying the peptoid by HPLC after filtration, dilution, and lyophilization.

Example 2 Specific Targeting Experiment of a Peptoid Molecular Probe in an EGFR-Overexpressing Cell Line The specific steps for cell-level imaging using a fluorescently labeled molecular probe with a peptoid were as follows:
(1) Cell culture and passage: The cell model was A549 cell line with high expression of EGFR protein and human embryonic kidney 293T cell line with low expression of EGFR (Shanghai Biological Technology Co., Ltd. enzyme research.); A549 and 293T cells were cultured in a constant temperature incubator (5% $CO_2$) at 37° C. with RPMI1640 medium and DMEM/High glucose medium containing 10% fetal bovine serum and 1% penicillin and streptomycin, respectively;
(2) When the degree of cell fusion reached more than 90%, the cells were passaged. The medium was aspirated with a pipette, and the residual medium, cell debris and the like were washed away with PBS; 0.25% trypsin containing EDTA was then added to digest at 37° C. for 2 min; the medium containing serum was added to stop the digestion; the mixture was centrifuged at 1000 rpm for 5 min, and the cells gathered at the bottom of the centrifuge tube; the medium was aspirated and then new medium was added; the cells were aspirated, uniformly dispersed in the medium, and then counted;
(3) A549 and 293T cells were respectively seeded into a special dish for laser confocal microscopy with a number of $1 \times 10^5$ cells per dish, and cultured for 12 hours;
(4) The medium was removed, and then 200 µL of the medium containing a dye (Rhodamine B)-labeled peptoid molecular probe was added and incubated at 4° C. for 30 min;
(5) The cells were washed 3 times with serum-free medium; 1 µg/mL DAPI was then added to stain the nuclei for 15 min; the cells were again washed 3 times with PBS; and then the cells were immediately observed and photographed under a laser confocal microscope at a 100× oil immersion objective. All parameter settings of microscopes were the same for all the samples.

The test results were shown in FIG. 1. The left column was the observation result of 293T cells:
A was a photograph showing the cells obtained by staining the nucleus with 4',6-diamidino-2-phenylindole (DAPI);
B was a photograph obtained by adding a dye (Rhodamine B)-labeled peptoid probe, which proved that the probe was absent or almost absent on the surface of 293T cells; C was superposition of A and B photographs.

The right column was the observation result of A549 cells:
D was a photograph showing the cells obtained by staining the nucleus with DAPI;
E was a photograph obtained by adding a dye (Rhodamine B)-labeled peptoid probe, which proved that the probe was enriched on the surface of A549 cells with high expression of EGFR;
F was superposition of D and E photographs.

Significant red fluorescence was observed for A549 cells to which the peptoid of Example 1 was added, while 293T cells in the control group showed weak fluorescence or no fluorescence.

FIG. 1 shows that the peptoid molecular probe can specifically target the EGFR protein on the A549 membrane to achieve localization.

Example 3 Binding Ability Between Peptoid Molecular Probe and EGFR Protein

The specific steps to test the binding ability between peptoid probe and EGFR protein using surface plasmon resonance imaging technology were as follows:
(1) The peptoid of Example 1 was dissolved in $ddH_2O$ at a concentration of 1-1000 µM to prepare a peptoid molecular probe sample to be spotted at a gradient concentration of 1-1000 µM;
(2) The above-mentioned peptoid molecular probe samples were spotted on the surface of a 3D chip (PlexArray HT, Plexera Bioscience Inc., USA) with 3 spots per sample; the chip was incubated at 4° C. for 12 hours, and then washed sequentially with 10×PBS, 1×PBS, and ultrapure water; and then the chip was blocked with 1M aminoethanol hydrochloride for 30 minutes, washed 5 times with ultrapure water, and finally dried with clean nitrogen;
(3) Installing the chip on an SPRi instrument, measuring an SPRi angle and adjusting the SPRi angle to an optimal optical location. Relevant test points (including sample points and blank points) were selected in a detection region, and an experimental flow rate was set as 2 µL/s.
(4) PBS was selected as a buffer and introduced into the flow cell until the baseline was stable; and then detection was sequentially performed with the EGFR protein solution at a concentration of 2.2 µM, 1.1 µM, 0.55 µM, 0.28 µM, and 0.14 µM. The binding time was 300 seconds, and the dissociation time was 300 seconds. Between the detection of a concentration of the EGFR protein and the detection of a next concentration of the EGFR protein, phosphoric acid was introduced for regeneration.

Figure 2:
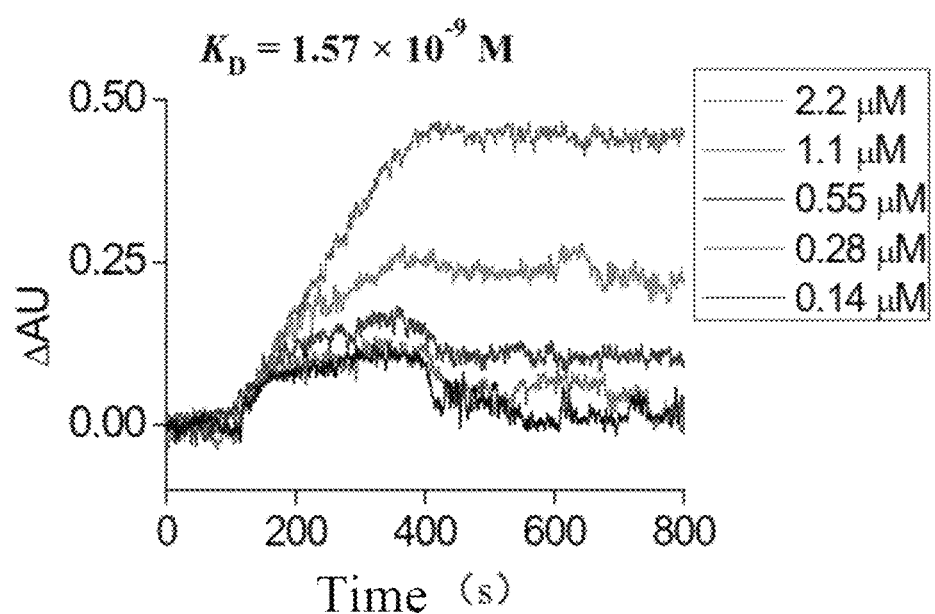
FIG. 2 is a graph showing the results of surface plasmon resonance detection of the peptoid of Example 1 bound to EGFR proteins at concentrations of 2.2 μM, 1.1 μM, 0.55 μM, 0.28 μM, and 0.14 μM.

The detection results are shown in FIG. 2. AAU represents an intensity of the binding signal calculated by deducting a baseline signal of the initial PBS buffer from the binding signal after the mobile phase passes the array, and the curve is obtained from a measurement of PlexArray HT. After fitting by BIA evaluation version 4.1 software (Biacore, Inc.), the equilibrium dissociation constant $K_D$ is $1.57 \times 10^{-9}$ mol/L, which indicates that the peptoid of Example 1 has a fairly high affinity with EGFR.

In summary, the molecular probe with peptoids disclosed herein is a molecule targeting probe with high sensitivity and affinity for EGFR protein, and provides a new option for targeted therapy or imaging detection of EGFR overexpressing lung cancer.

The present disclosure illustrates the process method disclosed herein through the above examples, but the present invention is not limited to the above process steps. That is, it does not mean that the present invention must rely on the above process steps to be implemented. In the case of no conflict, the examples disclosed herein and the features in the examples can be combined with each other to obtain new examples.

Those skilled in the art should understand that any improvement to the present invention, equivalent replacement of the raw materials used in the present invention, addition of auxiliary components, selection of specific manners, etc., all fall within the scope of protection and disclosure of the present invention. The protection scope of the present invention shall be defined by the claims.

What is claimed is:

1. A peptoid, which is a compound of Formula I, or a stereoisomer, a mixture of stereoisomers, or a pharmaceutically acceptable salt thereof,

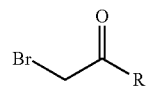

Formula I

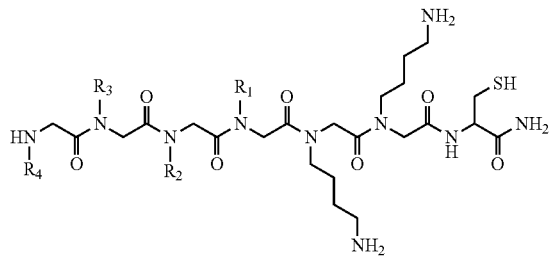

wherein N—$R_4$, N—$R_3$, N—$R_2$, and N—$R_1$ in Formula I are

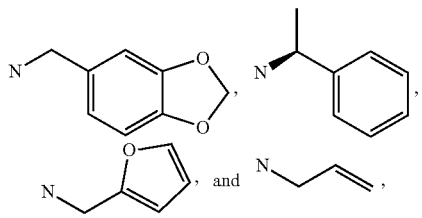

respectively.

2. The peptoid according to claim 1, wherein the pharmaceutically acceptable salt is hydrochloride, hydrobromide, sulfate, nitrate, phosphate, formate, acetate, propionate, fumarate, glycolate, pyruvate, malate, malonate, benzoate, cinnamate, mandelate, salicylate, maleate, citrate, succinate, tartrate, mesylate, ethanesulfonate, or p-toluenesulfonate.

3. The peptoid according to claim 1, which is the compound of Formula I.

4. A pharmaceutical composition comprising:
   the peptoid according to claim 1; and
   a pharmaceutically acceptable adjuvant.

5. The pharmaceutical composition according to claim 4, wherein the pharmaceutically acceptable adjuvant is any one or more of excipients, diluents, carriers, flavoring agents, binders, and fillers.

6. A pharmaceutical composition comprising:
   the peptoid according to claim 2; and
   a pharmaceutically acceptable adjuvant.

7. A pharmaceutical composition comprising:
   the peptoid according to claim 3; and
   a pharmaceutically acceptable adjuvant.

8. A method for imaging detection or prognostic monitoring of a cancer associated with EGFR protein, comprising administering the pharmaceutical composition according to claim 4, labeled with flurorphore.

9. The method according to claim 8, wherein the disease associated with EGFR protein is breast cancer, kidney cancer, colon cancer, rectal cancer, lung cancer, ovarian cancer, head and neck cancer, bladder cancer, pancreatic cancer, or glioma.

10. The method according to claim 9, wherein the disease associated with EGFR protein is non-small cell lung cancer.

11. A method for preparing the peptoid according to claim 1, comprising:
   (1) carrying out an amidation reaction between a compound of Formula II and an amino group at a terminal end of a solid phase support resin to form an amide bond;

Formula II

Br—CH$_2$—C(=O)—R wherein R is OH or Cl;
   (2) adding a monomer to replace the bromine atom through a nucleophilic substitution reaction;
   (3) repeating steps (1) and (2) until the synthesis of all subunits is completed,
   wherein the monomers are added in an order of cysteine, monoprotected tetramethylenediamine, monoprotected tetramethylenediamine, allylamine, 2-aminomethylfuran, α-methylbenzylamine, and 3,4-methylenedioxybenzylamine, wherein the wording "monoprotected" means that one amino group in the diamine is protected by an amino protecting group; and
   (4) removing the amino protecting group on the side chain, and cleaving the peptoid from the resin.

12. The method according to claim 11, wherein the α-methylbenzylamine used is R(+)-α-methylbenzylamine.

13. A chip comprising the peptoid according to claim 1.

14. The chip according to claim 13, wherein the peptoid is coupled to a surface of the chip.

15. The chip according to claim 13, wherein the chip is a microfluidic chip.

16. A kit for identifying circulating tumor cells, comprising: a box body, and the chip according to claim 15 disposed in the box body.

17. A method for detecting circulating tumor cells, comprising contacting the chip of claim 13 with a biological sample.

* * * * *